United States Patent [19]

Stähle et al.

[11] 4,215,133
[45] Jul. 29, 1980

[54] 2-[N-(2'-CHLORO-4'-METHYL-THIENYL-3')-N-(CYCLOPROPYL-METHYL)-AMINO]-2-IMIDAZOLINE AND SALTS THEREOF

[75] Inventors: Helmut Stähle; Herbert Köppe; Werner Kummer, all of Ingelheim am Rhein, Fed. Rep. of Germany; Walter Kobinger, Vienna, Austria; Christian Lillie, Vienna, Austria; Ludwig Pichler, Vienna, Austria

[73] Assignee: Boehringer Ingelheim GmbH, Ingelheim an Rhein, Fed. Rep. of Germany

[21] Appl. No.: 54,850

[22] Filed: Jul. 5, 1979

[30] Foreign Application Priority Data

Jul. 10, 1978 [DE] Fed. Rep. of Germany ....... 2830279

[51] Int. Cl.² .................. A61K 31/415; C07D 409/12

[52] U.S. Cl. .................. 424/273 R; 548/316; 548/348

[58] Field of Search ..................... 548/348; 424/273 R

[56] References Cited

U.S. PATENT DOCUMENTS

| 3,937,717 | 2/1976 | Stahle et al. ......................... 548/348 |
| 4,100,292 | 7/1978 | Stahle et al. ......................... 548/351 |

*Primary Examiner*—Natalie Trousof
*Attorney, Agent, or Firm*—Hammond & Littell, Weissenberger & Muserlian

[57] ABSTRACT

2-[N-(Cyclopropyl-methyl)-N-(2'-chloro-4'-methylthienyl-3')-amino]-2-imidazoline and non-toxic, pharmacologically acceptable acid addition salts thereof; the compounds are useful as bradycardiacs.

3 Claims, No Drawings

2-[N-(2'-CHLORO-4'-METHYL-THIENYL-3')-N-(CYCLOPROPYL-METHYL)-AMINO]-2-IMIDAZOLINE AND SALTS THEREOF

This invention relates to the novel compound 2-[N-(2'-Chloro-4'-methyl-thienyl-3')-N-(cyclopropylmethyl)-amino]-2-imidazoline and non-toxic acid addition salts thereof, to methods of preparing these compounds, to pharmaceutical compositions containing them as active ingredients, and to methods of using them as bradycardiacs.

More particularly, the present invention relates to the compound represented by the formula

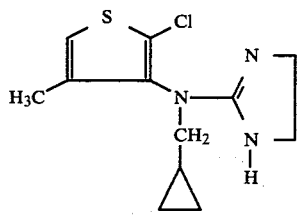

(I)

and non-toxic, pharmacologically acceptable acid addition salts thereof.

The compound of the formula I may be prepared by reacting 2-[N-(2'-chloro-4'-methyl-thienyl-3')-amino]-2-imidazoline of the formula

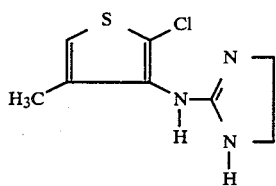

(II)

with a cyclopropyl-methyl halide of the formula

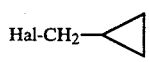

(III)

wherein Hal is chlorine, bromine or iodine.

In the alkylation of the compound of the formula II, the substitution is effected exclusively at the bridge nitrogen atom. The position of the substituent may be determined by NMR-spectroscopy. [cf H. Stähle et al, Liebigs Ann. Chem. 751, 159 et seq. (1971)].

It is advantageous to effect the reaction by heating the reaction partners, preferably in the presence of a polar or non-polar organic solvent, to temperatures of about 50° to 100° C. The specific reaction conditions depend to a great extent upon the reactivity of the reaction partners. It is recommended to provide the halide for the alkylation in excess and to perform the reaction in the presence of an acid-binding agent.

The starting compound of the formula II is disclosed in German Auslegeschrift No. 1,941,761.

The starting compounds of the formula III may be prepared by halogenating the corresponding primary alcohol.

The compound embraced by formula I is an organic base and therefore forms acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methane-sulfonic acid, 8-chlorotheophylline or the like.

The following examples illustrate the present invention and will enable others skilled in the art to understand it more completely. It should be understood, however, that the invention is not limited solely to the particular examples given below.

EXAMPLE I

2-[N-(Cyclopropyl-methyl)-N-(2'-chloro-4'-methyl-thienyl-3')-amino]-2-imidazoline A mixture consisting of 2.6 gm (0.012 mol) of 2-[(2'-chloro-4'-methyl-thienyl-3')-amino]-2-imidazoline (m.p. 152° C.), 1.4 gm (125% of the stoichiometrically required amount) of chloromethyl-cyclopropane and 20 ml of absolute ethanol was refluxed for about 20 hours, while stirring. Thereafter, the solvent was evaporated in vacuo, the residue was dissolved in dilute hydrochloric acid (just acid to Congo Red), and the solution was extracted twice with 50 ml each of ether. The ethereal extracts were discarded. The acid aqueous phase was then fractionally extracted with ether at stepwisely increasing pH-values (addition of 0.25 mll of 2 N sodium hydroxide at each step, until distinct alkaline reaction), which yielded about 15 ethereal fractions. Those fractions which contained the desired compound in pure form, as determined by thin-layer chromatography [mobile system: Benzene:dioxane:ethanol:concentrated ammonia=50:40:5:5; visualization:iodoplatinate; carrier:silicagel—G prefabricated plates, Merck No. 60 F 254; Rf=0.2 (comparison: Rf tiamenidine=0.6)], were combined, dried over magnesium sulfate, and evaporated in vacuo. 0.85 gm (26.1% of theory) of 2-[N-(cyclopropyl-methyl)-N-(2'-chloro-4'-methyl-thienyl-3')-amino]-2-imidazoline, m.p. 105°–108° C., was obtained.

| Elemental analysis: $C_{12}H_{16}ClN_3S$ (269.78) | | | | | |
|---|---|---|---|---|---|
| | C | H | Cl | N | S |
| Calc.: | 53.42% | 5.98% | 13.14% | 15.57% | 11.89% |
| Found: | 53.91% | 6.04% | 13.10% | 15.24% | 11.67% |

The compounds of the present invention, that is, the compound of the formula I above and its non-toxic, pharmacologically acceptable acid addition salts have useful pharmacodynamic properties. More particularly, they exhibit bradycardiac activity in warm-blooded animals, such as rabbits and rats, and are therefore useful for the treatment of coronary diseases.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0016 to 1.33 mgm/kg body weight, preferably 0.016 to 0.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 2

Coated Pills

The pill core composition is compounded from the following ingredients:

| | |
|---|---|
| 2-[N-(Cyclopropyl-methyl)-N-(2'-chloro-4'-methyl-thienyl-3')-amino]-2-imidazoline | 5 parts |
| Lactose | 65 parts |
| Corn starch | 130 parts |
| Secondary calcium phosphate | 40 parts |
| Soluble starch | 3 parts |
| Magnesium stearate | 4 parts |
| Colloidal silicic acid | 4 parts |
| Total | 250 parts |

Preparation:

The active ingredient is admixed with a portion of the excipients, the mixture is thoroughly kneaded with an aqueous solution of the soluble starch, the moist mass is granulated through a screen, and the granulate is dried. The dried granulate is admixed with the remainder of the excipients, and the composition is compressed in 250 mgm-pill cores which are subsequently coated with a thin shell consisting essentially of a mixture of sugar, talcum and gum arabic. Each coated pill is an oral dosage unit composition containing 5 mgm of the active ingredient.

EXAMPLE 3

Hypodermic Solution

The solution is compounded from the following ingredients:

| | |
|---|---|
| 2-[N-(Cyclopropyl-methyl)-N-(2'-chloro-4'-methyl-thienyl-3')-amino]-2-imidazoline | 1.0 part |
| Sodium chloride | 18.0 parts |
| Distilled water q.s.ad | 2000.0 parts by vol. |

Preparation:

The active ingredient and the sodium chloride are dissolved in the distilled water, the solution is filtered until free from suspended particles, and the filtrate is filled under aseptic conditions and in an atmosphere of nitrogen into 2 cc-ampules which are then sterilized and sealed. The contents of each ampule are an injectable dosage unit composition containing 1 mgm of the active ingredient.

EXAMPLE 4

Drop Solution

The solution is compounded from the following ingredients:

| | |
|---|---|
| 2-[N-(Cyclopropyl-methyl)-N-(2'-chloro-4'-methyl thienyl-3')-amino]-2-imidazoline | 0.02 parts |
| Methyl p-hydroxy-benzoate | 0.07 parts |
| Propyl p-hydroxy-benzoate | 0.03 parts |
| Demineralized water q.s.ad | 100.0 parts by vol. |

Preparation:

The active ingredient and the p-hydroxy-benzoates are dissolved in the demineralized water, the solution is filtered, and the filtrate is filled into 100 ml-bottles equipped with a dropping spout. 10 cc of the solution are an oral dosage unit composition containing 2 mgm of the active ingredient.

A non-toxic, pharmacologically acceptable acid addition salt of the active ingredient may be substituted for the free base in Examples 2 through 4. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 2-[N-(Cyclopropyl-methyl)-N-(2'-chloro-4'-methyl-thienyl-3')-amino]-2-imidazoline or a non-toxic, pharmacologically acceptable acid addition salt thereof.

2. A bradycardiac pharmaceutical dosage unit composition consisting essentially of an inert pharmaceutical carrier and an effective bradycardiac amount of a compound of claim 1.

3. The method of slowing the heart rate of a warm-blooded animal in need thereof, which comprises perorally or parenterally administering to said animal an effective bradycardiac amount of a compound of claim 1.

* * * * *